(12) United States Patent
Simms, Jr.

(10) Patent No.: US 9,067,073 B2
(45) Date of Patent: Jun. 30, 2015

(54) METHOD AND APPARATUS FOR STORING UP-TO-DATE INFORMATION ON AN IMPLANTABLE MEDICAL DEVICE

(71) Applicant: Cardiac Pacemakers, Inc., St. Paul, MN (US)

(72) Inventor: Howard D. Simms, Jr., Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/270,170

(22) Filed: May 5, 2014

(65) Prior Publication Data

US 2014/0330347 A1 Nov. 6, 2014

Related U.S. Application Data

(60) Provisional application No. 61/819,711, filed on May 6, 2013.

(51) Int. Cl.
| | | |
|---|---|---|
| *A61N 1/37* | (2006.01) | |
| *A61N 1/372* | (2006.01) | |
| *A61N 1/05* | (2006.01) | |
| *A61B 5/00* | (2006.01) | |
| *A61B 19/00* | (2006.01) | |
| *A61N 1/08* | (2006.01) | |
| *G06F 19/00* | (2011.01) | |

(52) U.S. Cl.
CPC ........ *A61N 1/37217* (2013.01); *A61N 1/37211* (2013.01); *A61N 1/37288* (2013.01); *A61N 1/37282* (2013.01); *A61N 1/05* (2013.01); *A61B 5/0031* (2013.01); *A61B 19/44* (2013.01); *A61N 1/0551* (2013.01); *A61N 1/056* (2013.01); *A61N 1/08* (2013.01); *A61N 1/37* (2013.01); *G06F 19/3418* (2013.01); *A61B 2019/448* (2013.01); *A61B 2562/08* (2013.01)

(58) Field of Classification Search
None
See application file for complete search history.

(56) References Cited

U.S. PATENT DOCUMENTS

| | | |
|---|---|---|
| 7,239,916 B2 | 7/2007 | Thompson et al. |
| 7,240,833 B2 | 7/2007 | Zarembo |
| 7,429,920 B2 | 9/2008 | Smythe et al. |
| 7,857,760 B2 | 12/2010 | Brister et al. |

(Continued)

OTHER PUBLICATIONS

Hsu, Lun-Chen, et al., "Nanofabricated Sensing Electrodes in a Batteryless Endoluminal Sensing Telemeter for Diagnosis of Gastroesophageal Reflux Disease (GERD)", ASME 2010 First Global Congress on NanoEngineering for Medicine and Biology, (Feb. 7-10, 2010), 2 pgs.

*Primary Examiner* — Kennedy Schaetzle
(74) *Attorney, Agent, or Firm* — Schwegman Lundberg & Woessner, P.A.

(57) ABSTRACT

Systems and methods are described for communicating device information and performance information associated with a population of other electrodes to a remote transceiver. The system can include a radio frequency identification (RFID) circuit coupled to an implantable component. The RFID circuit can include a memory circuit configured to store device information associated with at least one implantation-independent attribute of the implantable component. The RFID circuit can communicate the device information and performance parameters associated with the implantable component to at least one programming unit such as a remote transceiver. The programming unit can program the RFID circuit with information associated with the implantable component.

20 Claims, 8 Drawing Sheets

(56) References Cited

U.S. PATENT DOCUMENTS

| | | |
|---|---|---|
| 7,932,825 B2 | 4/2011 | Berger |
| 7,983,763 B2 | 7/2011 | Stevenson et al. |
| 8,223,021 B2 | 7/2012 | Goodnow et al. |
| 8,253,555 B2 | 8/2012 | Stevenson et al. |
| 8,299,899 B2 | 10/2012 | Frysz et al. |
| 2008/0065181 A1* | 3/2008 | Stevenson ............... 607/115 |
| 2010/0161003 A1* | 6/2010 | Malmberg et al. ........... 607/60 |
| 2011/0021887 A1 | 1/2011 | Crivelli et al. |
| 2011/0022411 A1* | 1/2011 | Hjelm et al. ................ 705/2 |
| 2014/0049377 A1* | 2/2014 | Krusor et al. ............. 340/10.1 |

* cited by examiner

METHOD AND APPARATUS FOR STORING UP-TO-DATE INFORMATION ON AN IMPLANTABLE MEDICAL DEVICE

CLAIM OF PRIORITY

This application claims the benefit of priority under 35 U.S.C. §119(e) of U.S. Provisional Patent Application Ser. No. 61/819,711, filed on May 6, 2013, which is herein incorporated by reference in its entirety.

BACKGROUND

An implantable medical device (IMD) such as a pacemaker, a defibrillator, or other electrostimulation device can be programmed by a healthcare provider such as a physician to acquire diagnostic information from a patient and/or to provide therapy to a patient. Generally, a programming unit ("PU") can be provided to the healthcare provider to program the IMD. The PU may be pre-programmed with software configured to inform or guide the healthcare provider to provide therapy to the patient that is adapted to a particular use scenario.

An automated identification and configuration system was developed for use with an IMD as discussed in U.S. Pat. No. 7,239,916 entitled, "Method and Apparatus for Automatic Implantable Medical Lead Recognition and Configuration." In that approach, a detachable component includes a readable memory circuit that can convey identification information to an IMD. The identification information can be used to customize the therapy, but is limited to the information pre-programmed into the lead.

An identification device for an implantable lead is discussed in U.S. Pat. No. 7,983,763 entitled, "Implanted Lead Sleeve having RFID Tag." In that approach, an RFID tag includes identification information relating to the implantable lead, its associated lead system, or an associated implantable medical device, enabling wireless discovery of information pre-programmed into the lead.

OVERVIEW

The programming unit ("PU"), by executing software, may recognize that the IMD has sensed or otherwise recorded certain use characteristics, and suggest, enable, or otherwise alert a healthcare provider to provide therapy adapted to a patient's condition. Often these use characteristics are unique to the IMD or the associated components such as one or more leads coupled to the IMD. When the IMD or the associated components are explanted, revised, or replaced, this adapted information can be lost, which can affect system performance. To address this problem, information can be stored in detachable components such as leads. The information can be used by an IMD or a PU to alter therapy when specified conditions are met.

The present inventors have recognized, among other things, that the approaches mentioned in the Background section do not provide these benefits, and otherwise suffer from several shortcomings. First, it can be difficult to preserve performance attributes associated with the IMD-lead combinations. This is apparent in situations in which a programming unit, other than the initially used programming unit, is used with an implanted component such as a lead. For example, in a first surgery, a first IMD and a first lead may be implanted and programmed with a PU, such as a custom or proprietary PU. Later, such as during a second surgery, the IMD may be replaced with a new IMD, such as a different model IMD, perhaps made by a different manufacturer, while the lead may remain implanted (e.g., at least because it is ingrown into an target site). A new PU may be used with the new IMD. Because the original IMD is explanted and discarded, performance attributes learned and stored on that IMD may be lost. This can be compounded if the original PU did not communicate information with a replacement PU.

Second, the performance of the IMD or the associated components may have been calibrated during the research and development phase of device creation, before certain use cases have been experienced. Such use cases may be associated with attributes of the equipment not appreciated during initial calibration. While an implantable lead may be considered to have a desired performance at the outset, improved, or even optimum, performance may ultimately fall outside of that range.

Third, these approaches merely facilitate identification of a component such as a lead or IMD. However, these approaches do not sufficiently provide performance data associated with the implantable medical system including the IMD or the lead. Typically, the device performance data, such as desirable range of impedance for a particular type of lead, can be stored in the IMD or a dedicated transceiver such as a programmer. With the increasing volume and varieties of device performance data (such as data from various types of leads that can be used with the IMD), storing the device performance data in the IMD or the programmer can become very complex and expensive. Additionally, when a lead or an IMD is explanted and a new lead or a new IMD is implanted, device performance data such as lead impedance or pacing threshold can be lost. Therefore, the present inventors have recognized that there remains a need of devices and methods to incorporate flexibility in systems such that different models of the IMD or the associated components can be used to their full potential.

The present subject matter can help provide solutions to these identified problems. The systems and methods described in this document can automatically record up-to-date, implantation-independent attributes or specific performance related information from different models of IMD or associated components, onto associated components. By way of example, the present document describes systems and methods for storing information, such as implantation-independent attributes or performance information associated with one or more performance parameters, in an IMD or one or more associated components such as leads. The information stored can include population-sourced information. This can be beneficial such as when low cost, increased flexibility, and reduced training requirements may need to be fulfilled for configuration and performance monitoring of the IMDs or the associated implantable components.

In an example, this document describes a system for implantation into a target site. The system can include an implantable electronics unit including a biocompatible exterior portion, an electronic circuit, and at least one radio frequency identification (RFID) circuit, that can form a tag, attached to the implantable electronics unit. The electronic circuit can include device information associated with an implantation-independent attribute of the implantable electronics unit. The electronic circuit can also include performance information associated with a population of other implantable electronics unit in use external to the target site. The at least one RFID circuit can communicate with the electronic circuit, and communicate the device information and the performance information to a remote transceiver during interrogation.

A method can include coupling a RFID circuit to an implantable electronics unit such as an IMD or any associated components such as one or more leads, storing in the RFID circuit device information associated with at least one implantation-independent attribute of the implantable electronics unit, storing the performance information associated with performance parameter associated with a population of other implantable electronics unit in use with a separate implantable electronics unit. The method includes identifying the RFID circuit such as with a remote transceiver. Upon identification of the RFID circuit, information stored in the RFID circuit, including device information and performance information, can be communicated to the remote transceiver.

A method can include communicating an implantation-independent attribute of an implantable medical lead to a remote transceiver. The method can include coupling a memory circuit, such as an RFID circuit, to an implantable medical device lead, and storing an executable program, associated with the implantable medical device lead, in the RFID circuit. The method can include storing in the RFID circuit performance information associated with a population of other electrodes in use, and identifying the RFID circuit with the remote transceiver. Upon identification of the RFID circuit, the method can include communicating the at least one implantation-independent attribute to the remote transceiver. The method can include transacting the executable program to other devices as well.

This overview is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE FIGURES

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Disclosed herein are systems and methods that can provide information about an implantable device, including device information (e.g., engineering specifications) and performance information (e.g., performance of a field population). Such information can include one or more attributes of an implantable medical device (IMD) or attributes of associated components coupled to the IMD (e.g., a passive and/or non-therapeutic device including, but not limited to, leads, cuffs, patches, remote self-contained sensors and the like). The attributes can be independent of an implantation of the device.

The device information and the population performance information can be stored in a memory circuit in a radio frequency identification (RFID) circuit attached to the IMD or the associated components. The present systems and methods can read from the RFID circuit up-to-date population performance data related to the IMD or the associated components and provide the data to the healthcare provider. Through the use of the up-to-date population performance data, the present systems and methods can improve patient monitoring and assist the healthcare provider to choose appropriate device for the patient, or to program appropriate therapy for the patient.

Figure 1:
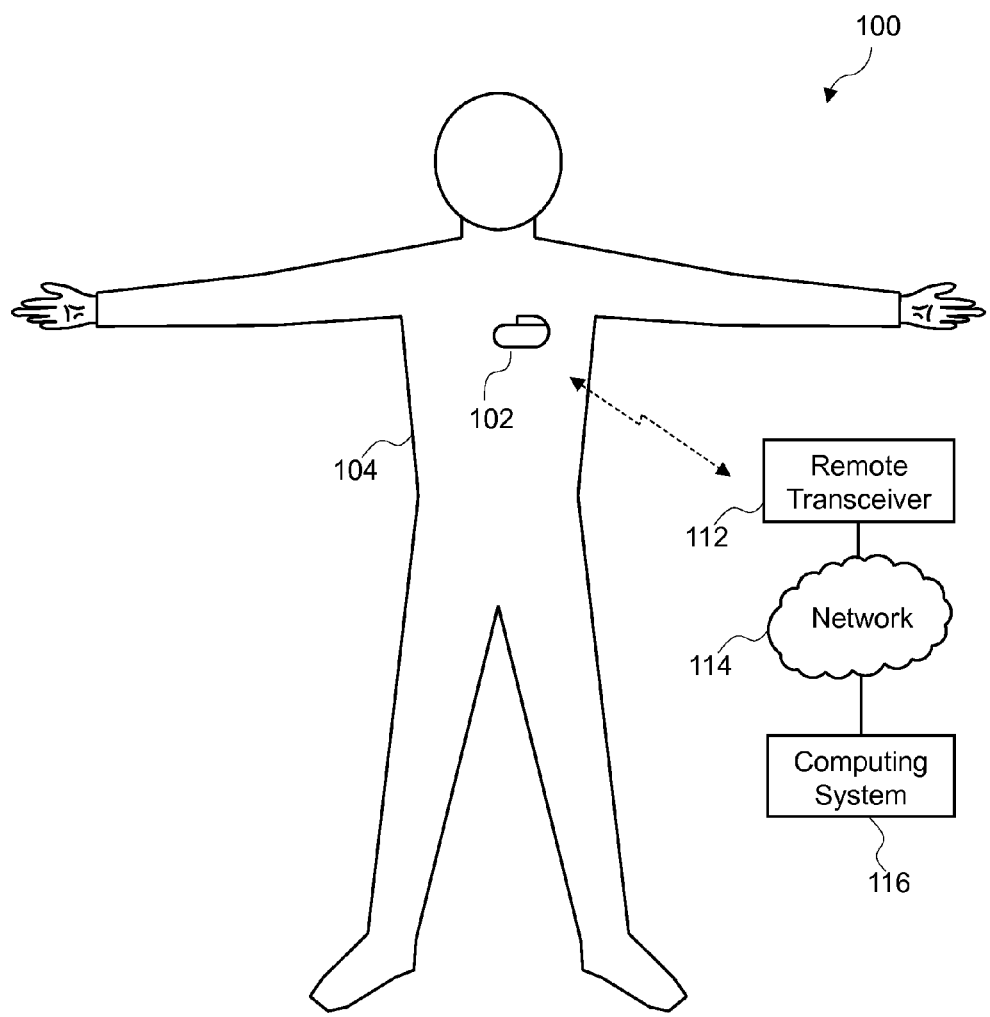
FIG. 1 illustrates an example of portions of an implantable medical system and an environment in which it can be used.

FIG. 1 illustrates an example of portions of an implantable medical system 100 and an environment in which the implantable medical system 100 can be used. The system 100 includes an implantable medical device (IMD) 102 that can be implanted within a patient 104 to treat one or more diseases or medical conditions of the patient 104. Example of the IMD 102 can include implantable cardiac pacemakers, cardioverter/defibrillators, drug delivery systems, cardiomyopathy stimulators, cardiac and other physiologic monitors, electrical stimulators including nerve and muscle stimulators, deep brain stimulators, cochlear implants, heart assist devices or pumps, and other implantable devices. The IMD 102 can be a deep brain stimulator that provides therapy to the patient 104 to treat neurological disorders such as Parkinson's disease, essential tremor, chronic pain, and the like.

The implantable medical system 100, including the IMD 102 and one or more associated components, can be implanted within the patient 104. The associated components of the IMD 102 can include one or more leads, one or more physiological sensors, or any other such components. A deep brain stimulator system can include a pulse generator and associated components such as one or more electrodes coupled to the pulse generator through one or more leads, or one or more sensors such as to deliver a stimulation therapy to one or more portions of the brain of the patient 104. A cochlear implant system can include a nerve stimulator and associated components such as one or more acoustical transducers, a sound processor, a power source, and one or more electrodes such as for delivering an electrical stimulation therapy to a nerve such as an auditory nerve.

The implantable medical system 100 can be configured to include or couple to a memory circuit such as with one or more radio frequency identification (RFID) circuits. The memory circuit in the RFID circuits can be configured to store information including patient information, device information, performance information, or combinations thereof. Such information can be associated with the patient 104 or the IMD 102. The patient information can include patient name, address, medical history, demographical information, treating physician and institution, implanted device history, or any other information for the assistance of the physician. The device information can include the manufacturer, type, composition, dimensions, geometric configurations, date of implantation, expiration date if applicable, type of instruments required for removal of the IMD 102, or other information that can be beneficial for a physician to program effective therapy for the patient 104. The performance information of the implantable system can include threshold values or pre-determined value range that can affect the performance of the implantable system, such as upper or lower limits of sensing values or pacing threshold for a particular electrode on a lead associated with the IMD 102. The performance information can also include performance parameters for a population of electrodes associated with the IMD 102. Based on the performance information, the physician can perform performance evaluations and decisions regarding operability of the implantable system.

The IMD 102 can be configured to communicatively couple to a remote transceiver 112 through a communication link. Such a link can be wireless or wired. Wireless communication can include at least one of near-field and far-field communication. Communication links can include, but are not limited to, an inductive telemetry link, a radio frequency (RF) telemetry link, and a telecommunication link such as a satellite communication link or internet connection. The remote transceiver 112 can include a programmer or a programming unit (PU) configured to, upon receiving a command such as during an interrogation, communication information via RFID circuits. The remote transceiver 112 can program the RFID circuits via the communication link. The remote transceiver 112 can read from the RFID circuit the performance information associated with one or more performance parameters that can include up-to-date performance corresponding to the IMD 102 or the one or more associated components, such as an up-to-date impedance between two specified electrodes on a lead attached to the IMD 102.

As illustrated in FIG. 1, the remote transceiver 112 can be connected to a computing system 116 through a network 114. The remote transceiver 112 can be a portion of a computing system 116. The computing system 116 can include a remote patient management system that can be configured to remotely monitor the patient 104 or control the operations of the IMD 102 such as by using the performance information as available in the RFID circuits attached to the IMD 102 or to the one or more associated components of the IMD 102.

The computing system 116 can be configured to access a database that can include population performance data from several devices of a type similar to the IMD 102, or from several components similar to the associated component of the IMD 102. The database can be configured to include population performance data of a particular type of lead, where the population performance data can be collected over a period of time over a range of leads having characteristics similar to the lead associated with the IMD 102. The population performance data can be derived from various sources including, but not limited to, clinical trials of the particular component, extracted data of the same or similar explanted or out of service components, recommended performance values from various physicians or experts, records or data based on past usage of similar devices or any other source. The population performance data can be stored in the RFID circuit while manufacturing of the IMD 102 or the particular component. The computing system 116 can be configured to utilize the remote transceiver 112 to update the RFID circuit with the population performance data using the near-field or far-field wireless communication link.

The population performance data of the particular component can be provided by the RFID circuit to assist the physician during a medical procedure. The population performance data can include information such as malfunctions of an electrical component, an electrical connection, battery, high volcircuite capacitor, software or firmware, mechanical connection, and the like for a particular model of the IMD 102. The computing system 116 can be configured to provide the population performance data to a healthcare provider such as a physician.

The computing system 116 can further be configured to compare the population performance data to the performance data of the component under consideration so as to reasonably conclude about the performance of the component under consideration. The computing system 116 can include various tools to assess and control the performance of the component under consideration relative to the population performance, such as range setting (lower and upper limits of performance), median, sampling solutions, analysis of variance (ANOVA), analysis of covariance (ANCOVA), standard deviation and other measurements or statistical methods. Based on the comparison, the computing system 116 can recommend or assist the healthcare provider to evaluate or choose a particular type of IMD or an associated component, to decide on whether to replace the IMD 102 or any of its associated component with a new IMD or a new associated component, or to reprogram the IMD 102 or reconfigure the associated component such as to improve the efficacy of therapy to the patient 104.

Figure 2:
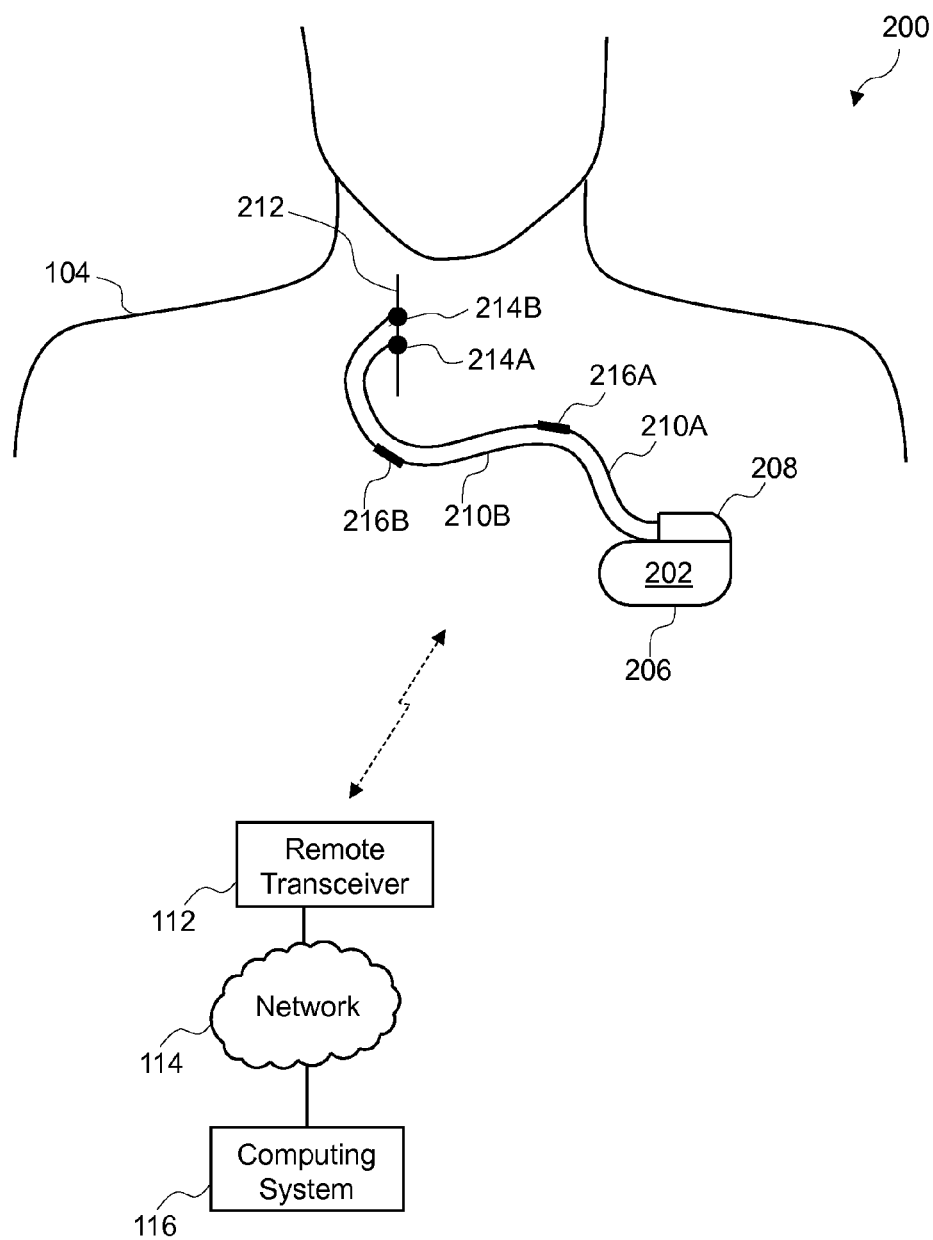
FIG. 2 illustrates an example of portions of a neural stimulation therapy system configured to use data associated with a radio frequency identification (RFID) circuit.

FIG. 2 illustrates an example of portions of a neural stimulation therapy system 200 configured to use data associated with one or more RFID circuits 216 (216A, 216B). The neural stimulation therapy system 200 can be configured to include an IMD 202 that can be used to deliver a neural stimulation therapy (NST) to the patient 104 such as by using the performance data of the components stored in the RFID circuits 216. The IMD 202 can be configured to deliver the NST to one or more bodily tissues of the patient 104 to treat various disorders such as sleep-disordered breathing, hypertension, heart failure, epilepsy, depression, pain, migraines, eating disorders, obesity, inflammatory diseases, movement disorders, and the like.

The IMD 202 can include a hermetically-sealed housing 206 and a header 208 extending from the housing 206. The header 208 of the IMD 202 can include one or more receptacles for receiving proximal ends of leads 210 such as a lead 210A and a lead 210B. The distal ends of the leads 210 can include one or more electrodes for use in delivering stimulation pulses to a neural target 212 of the patient 104. Examples of the neural target 212 include the vagus nerve, nerve bundles, nerve trunks, and other neural targets. The distal end of the lead 210A can include an electrode 214A and the distal end of the lead 210B can include an electrode 214B (one or more of these electrodes are collectively referred to hereinafter as electrodes 214). The electrodes 214 can be configured to deliver stimulation pulses to respective sites of the vagus nerve 212. The housing 206 of the IMD 202 can include a reference electrode (e.g., a "can" or housing electrode), and the neural stimulation can be delivered using one or more electrodes selected from the lead electrodes 214 and the reference electrode of the housing 206.

As illustrated in FIG. 2, the RFID circuits 216 can be coupled to the respective leads 210 such as to store information associated with the leads 210 and other components disposed on the leads such as the electrodes. The RFID circuits 216 can include population performance data associated with various performance parameters of the leads 210 or the electrodes 214 of the respective leads.

The performance parameters can include various configurations, specifications, and factors that can influence performance and functioning of the components such as the leads or the electrodes. The performance parameters can include electrical physiologic measurements such as sensing values (such as P-wave or R-wave amplitude from a sensed electrogram), pacing threshold values (such as pacing amplitude, pulse width, frequency, duty cycle) that can evoke tissue depolarization, impedance values between electrodes, among others. The performance parameters can include mechanical or chemical physiologic measurements such as stress, strain, movement, pressure, chemical composition, ionic content, blood assay, among others. The RFID circuits 216 can be associated with any other component or components in the same IMD 202 such as to monitor performance of several components at the same time.

The remote transceiver 112 can be configured to extract the stored information such as the population performance data from the RFID circuit 216 through a wired or a wireless communication link. The remote transceiver 112 can extract the information from the RFID circuit 216 upon receiving a command such as during an interrogation. The remote transceiver 112 can also be configured to program or reprogram the IMD 202 for delivering the neural stimulation therapy to the neural target 212 of the patient 104. Historical performance data of the components being monitored can be added to the population performance data to further refine the population performance data. The up-to-date population performance data can be stored in the RFID circuits 216.

The delivery of neural stimulation therapy to the vagus nerve 212 of the patient 104 can include delivering stimulation pulses of varying pulse characteristics to the vagus nerve 212. The RFID circuits 216 can be configured to include performance data associated with the varying characteristics of the stimulation pulses. The performance data can include characteristics, including but not limited to, pulse width, pulse frequency, duty cycle of the pulses, timing for delivery of pulses, pulse amplitude or any other such characteristic. The varying pulse characteristics can cause the electrodes to perform differently across a population of electrodes. For example, varying the stimulation pulse amplitude can cause different electrode potentials that can elicit different physiological responses in the body of the patient 104. Some of these physiological responses can be desirable, such as heart rate variation, laryngeal vibration and the like, while some physiological responses can be undesirable, such as coughing or pain. The RFID circuits 216 can be configured to include performance information related to the elicitation of various types of physiological responses at different sites in the body of the patient 104 at different electrode potentials. This can help the physician such as at the time of configuring a programmer to deliver the neural stimulation therapy to the patient 104. The physician can obtain the performance related information associated with electrode potentials from the RFID circuits 216 and can adjust the therapy accordingly, so as to elicit only the desirable physiological responses in the patient 104. Similarly, several other contextual parameters that may influence the performance of the components may also be recorded while recording the performance data of the population so that an association between the performance data and the contextual parameters may facilitating in deciding as to what performance may be suitable or unsuitable in a particular context or in association with a particular set of parameters.

As illustrated in FIG. 2, the remote transceiver 112 can be connected to a computing system 116 through a network 114. The remote transceiver 112 can extract the performance information from the RFID circuits 216, and use the performance information to monitor the delivery of the neural stimulation therapy. The remote transceiver 112 can transmit the performance information to the computing system 116 through the network 114. The computing system 116 can comprise a display unit such as a monitor configured to present to an entity such as healthcare provider the information extracted from the RFID circuits 216, which can assist the physician to evaluate the performance of a the IMD 202, the leads 210, or other components associated with the IMD 202, and/or to monitor and adjust the therapy delivery. The computing system 116 can also include a database that can maintain the performance data collected across a population of electrodes.

Figure 3:
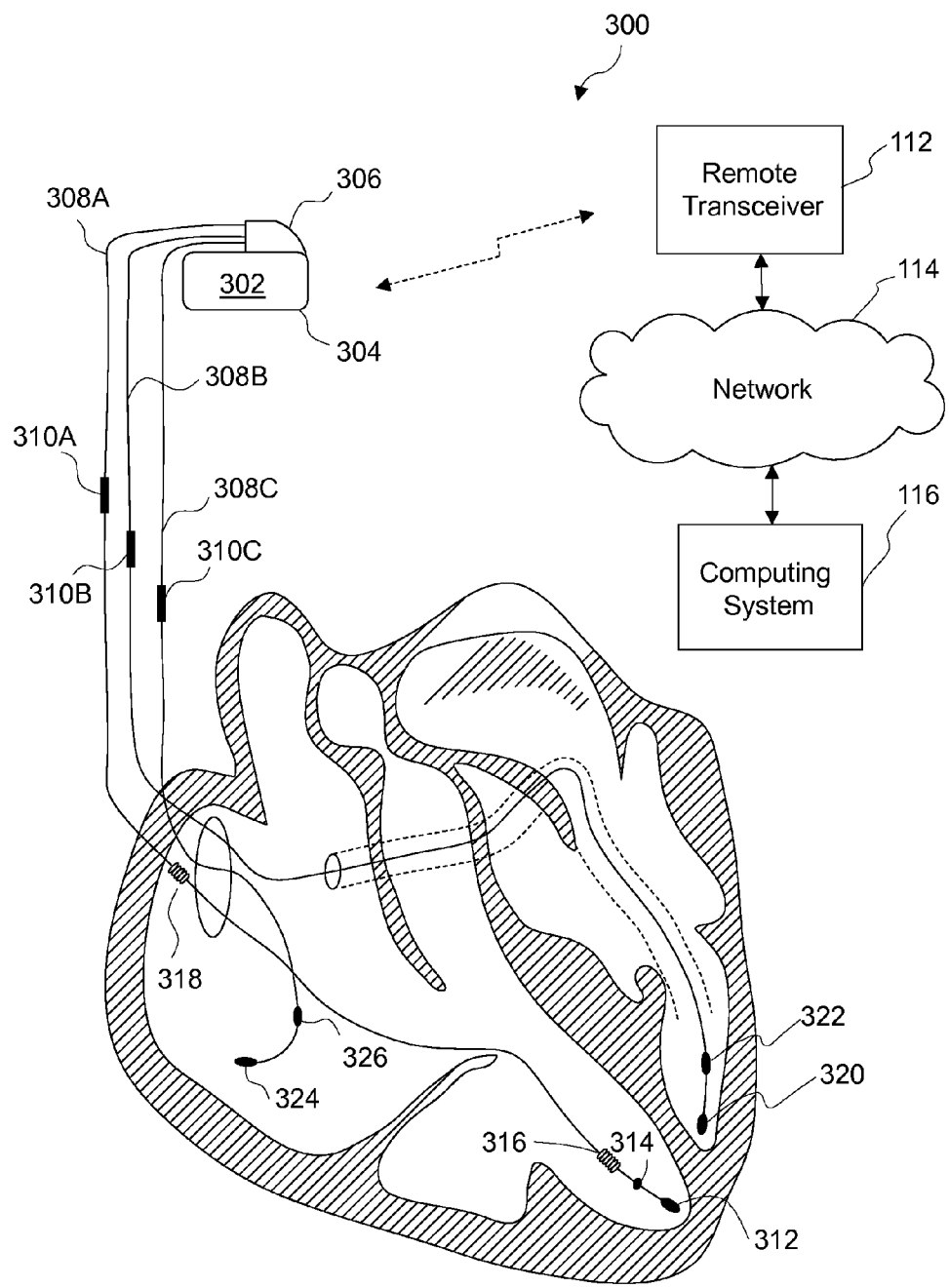
FIG. 3 illustrates an example of portions of a cardiac rhythm management (CRM) system configured to use data associated with the RFID circuit.

FIG. 3 illustrates an example of portions of a cardiac rhythm management (CRM) system 300 configured to use data associated with the RFID circuits 310 (310A, 310B and 310C). The CRM system 300 can be configured to include an IMD 302 that can be used in delivery of a CRM therapy to treat cardiac arrhythmias or to improve cardiac function such as in patients with heart failure using the performance data of the components stored in the RFID circuit 310. The IMD 302 includes a housing 304 and a header 306 that can include one or more receptacles for receiving proximal ends of one or more leads such as a lead 308A, a lead 308B, and a lead 308C (collectively referred to hereinafter as leads 308). The distal ends of the leads 308 can include one or more electrodes for use in providing pacing energy, defibrillation energy, or both, to a heart of the patient 104. The leads 308 and electrodes can be used to sense electrical activity of the heart, including electrical activity related to contractions of atria or ventricles of the heart.

The lead 308A can be an intravascular right ventricle (RV) lead that extends from a superior vena cava (SVC) into a right atrium (RA), and then into the RV. The lead 308A can include an RV tip electrode 312, a slightly more proximal RV ring electrode 314, a still slightly more proximal RV shock coil electrode 316, and a more proximal RA or SVC shock coil electrode 318. The lead 308B is an intravascular coronary sinus (CS)/left ventricle (LV) lead that extends from the SVC into the RA through the CS into the coronary vasculature, such as near a portion of the LV. The CS/LV lead 308B can include a distal electrode 320 and a proximal electrode 322 through which electro-stimulation energy can be delivered or intrinsic electrical heart signals can be sensed. The lead 308C can be an intravascular RA lead 308C that can extend from the SVC into the RA. The lead 308C can include a distal electrode 324 and a proximal electrode 326.

Other forms of electrodes can include meshes or patches that can be applied to the portions of the heart or which can be implanted in other areas of the body to help "steer" electrical currents produced by the IMD 302. The present methods and systems can work in a variety of configurations and with a variety of electrodes. The different implantable electrode configurations can include various combinations of sensing and stimulating pairs. For example, one electrode configuration (RA-can) can be set up by sending a stimulating current between RA-ring electrode and the housing 304 and sensing the resulting volcircuite between RA-tip electrode and the housing 304. A configuration can include RV-can configuration that utilizes electrodes on the RV lead 308A and the housing 304 for stimulation and sensing. A configuration can include LV-can (e.g., configuration utilizing electrodes on the LV lead 308B and the housing 304 for stimulation and sensing). Additional configurations can include RA-LV-can (e.g., configuration utilizing electrodes on the RA lead 308C, LV lead 308B and the housing 304 for stimulation and sensing), RV-LV (e.g., configuration utilizing electrodes on RV lead 308A and LV lead 308B for sensing and stimulating), and the like. The electrodes typically deliver cardioversion, defibrillation, pacing, resynchronization therapy, or combinations thereof to at least one portion of the heart.

As illustrated in FIG. 3, the leads 308 (such as the lead 308A, the lead 308B, or the lead 308C) can be configured to couple to the respective RFID circuits 310 (such as the RFID circuit 310A, the RFID circuit 310B, or the RFID circuit 310C). The RFID circuits 310 can be configured to store information such as population performance data including cardiac perforation, conductor fracture, lead dislodgement, failure to capture, over-sensing, failure to sense, insulation breach, abnormal pacing impedance, extra cardiac stimulation and the like for the respective leads. The RFID circuits 310 can be configured to communicate with the remote transceiver 112 using a wired or wireless link such as during an interrogation. The remote transceiver 112 can be configured to extract the information (such as the population performance data) stored in the RFID circuits 310. The remote transceiver 112 can be connected to a computing system 116 through a network 114, and provide the information extracted from the RFID circuits 310 to the computing system 116.

The computing system 116 can comprise a display unit such as a monitor configured to present to a healthcare provider such as a physician the information extracted from the RFID circuits 310. Such presentation can assist the physician to select an appropriate action for the respective lead such as to deliver the therapy to the patient. The information extracted from the RFID circuits 310 can include the population performance data such as indicating that a particular lead (e.g., 308A) has a relatively higher rate of extra cardiac stimulations. This information can assist the physician to decide whether to reject a particular lead (e.g., 310A) at least in part because of the high extra-cardiac stimulations. In an example, the RFID circuits 310 can be configured to store information associated with the impedance values for a variety of electrode configurations of the respective leads 308 at specific implantation sites. The remote transceiver 112 can assist the physician to automatically access the impedance values stored in the RFID circuit 310B when the lead 310B is configured in any one of the aforementioned configurations to deliver a cardiac resynchronization therapy (CRT) for treating bundle branch block or congestive heart failure. The RFID circuits 310 can be configured to store performance information such as pacing threshold values for the respective leads 308 so as to avoid any unwanted phrenic nerve stimulation during the delivery of the CRM therapy to the patient 104.

Figure 4A:
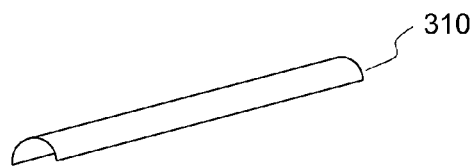
FIGS. 4A-4C illustrate examples of perspective views of an implantable lead adapted to be coupled with the RFID circuit.
Figure 4B:
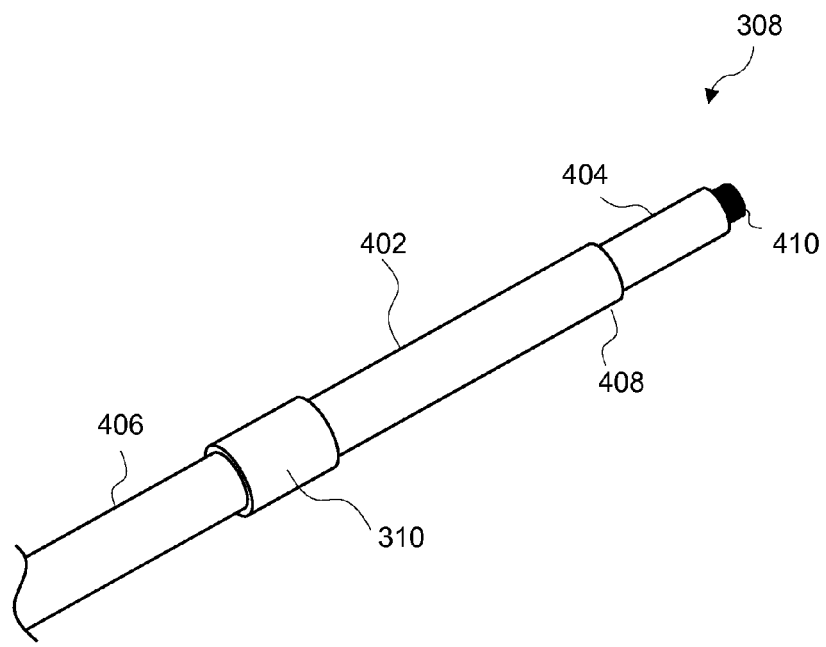
Figure 4C:
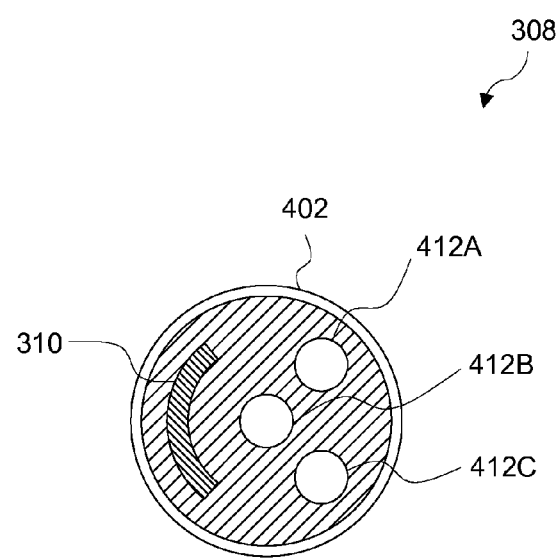

FIGS. 4A-4C illustrate examples of perspective views of respective embodiments of the implantable leads adapted to couple to the RFID circuit 310. Examples of the implantable leads include the leads 308 coupled to the IMD 302 that can provide CRM therapy, the implantable leads 210 coupled to the IMD 202 that can provide neural stimulation therapy, or other implantable catheters or leads for diagnostic or therapeutic purposes. The RFID circuit 310 can be contained in a hermetically sealed container such as to protect the RFID circuit 310 from the bodily fluids of the patient 104. The RFID circuit 310 can be sized, shaped or otherwise configured to conform to the shape or contour of the implantable lead where the RFID circuit 310 can be attached.

As illustrated in FIG. 4A, the RFID circuit 310 can be curled to conform to the shape of an exterior surface of the implantable lead 308 so that the RFID circuit 310 can be securely attached to the lead 308. The RFID circuit 310 can be packaged in the form of a cylindrical structure such as to establish the communication session with the remote transceiver 112 at a relatively lower radio frequency (e.g., approximately 125 kHz). The RFID circuit 310 can be packaged in the form of a thin film such as to enable communication at a relatively higher frequency. For example, the RFID circuit 310 can be packaged in the form of a thin rectangular strip for use at higher frequencies in a range of approximately 900 MHz to 2.4 GHz. The RFID circuit 310 can be adapted to conform to other shapes or geometries, such as a cubical geometry, an oval structure, a circular structure or any other such geometry so that the RFID circuit 310 can be attached to or included in other components of the IMD 302.

FIG. 4B shows a perspective view of the implantable lead 308 adapted to include the RFID circuit 310 on an outer surface of an elongated lead body 402. The outer surface of the elongated lead body 402 can be made of a biocompatible material such as to minimize accumulation of bodily fluids on the implantable lead 308. The implantable lead 308 can be configured to include one or more signal conductors 404 that can extend from a proximal portion 406 of the lead body 402 to a distal portion of the lead body 408. An electrode 410 can be affixed to the lead body 402. The electrode 410 can be configured to be in electrical communication with the signal conductor 404. The electrode 410 can be affixed to the distal portion 408, the proximal portion 406, or anywhere along the lead body 408. As illustrated in FIG. 4B, for the purpose of exemplary description, the RFID circuit 310 can be sized and shaped in the form of a cylindrical structure conforming to the exterior surface of the lead body 402. It can be positioned at a location close to the proximal portion 406 of the lead body 402. Other shapes, sizes, and configurations of the RFID circuit 310 have also been contemplated, and the RFID circuits 310 can be placed anywhere along the elongated lead body 402.

FIG. 4C shows a perspective view of another example of the implantable lead 308 adapted to include the RFID circuit 310 within the lead body 402. The lead body 402 can include a plurality of lumens 412, such as a lumen 412A, a lumen 412B, or a lumen 412C. The plurality of lumens 412 can extend from the proximal portion 406 of the lead body 402 to the distal portion 408 of the lead body 402. During an implantation of the implantable lead 308, a plurality of movable components such as wire conductors (not shown) may be inserted through the plurality of lumens 412 of the lead body 402. As shown in FIG. 4C, the RFID circuit 310 can be embedded within the lead body 402 for a specified thickness. The RFID circuit 310 can be disposed at various suitable locations with respect to the lead body 402. For example, the RFID circuit 310 can be placed over a periphery of the lead body 402 covering a portion of the lead body 402 circumferentially at least partially. The RFID circuit 310 can be disposed in the shape of a linear strip along a length of the lead body 402. The RFID circuit 310 can also be disposed along an inner surface of the lead body 402 circumferentially. The RFID circuit 310 can assume any other geometric shape to be configured to be attached to or embedded in the lead body 402.

The RFID circuit 310 is shown as an exemplary description to be included in the implantable lead 308. However, the present inventors have contemplated that the RFID circuit 310 can be employed to affix to any one or more components of an implantable medical system, including an IMD such as the IMD 102, the IMD 202, the IMD 302, or one or more components associated with the implantable device, as discussed in FIGS. 2 and 3.

Figure 5:
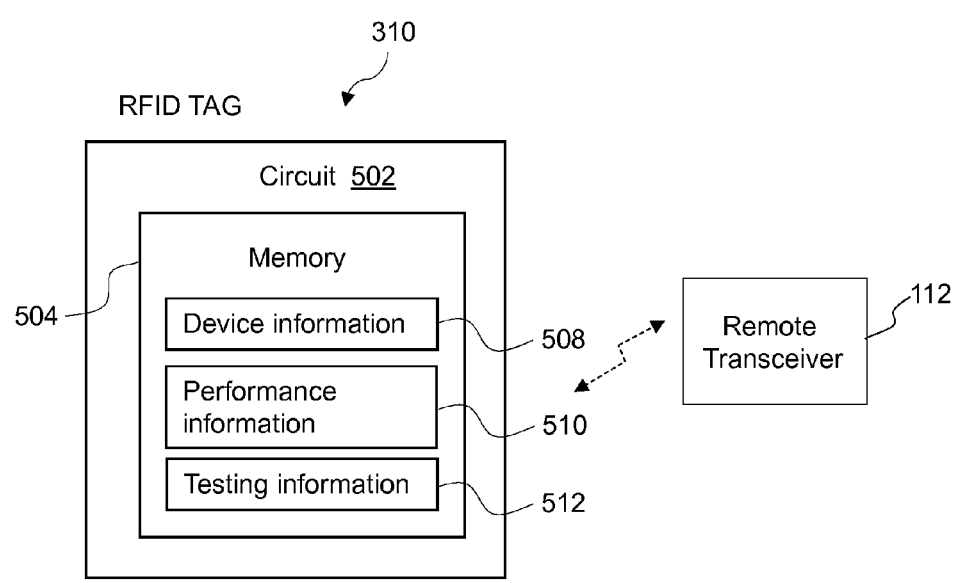
FIG. 5 shows a block diagram of the RFID circuit configured to communicate information with a remote transceiver, according to an example.

FIG. 5 shows a block diagram of the RFID circuit 310 that can be configured to communicate information with the remote transceiver 112, according to an example. The RFID circuit 310 can be configured to include a circuit 502 (referred to hereinafter as a RFID circuit) that can be adapted to include a memory 504 for storing device information 508, performance information 510, and testing information 512. The circuit 502 can be an electrode circuit adapted to be in electrical communication with the one or more electrodes of a lead such as the lead 308 or the lead 210. The RFID circuit 310 can be configured to communicate the device information 508, the performance information 510 and the testing information 512 to the remote transceiver 112 when the RFID circuit 310 is within a specified distance of the remote transceiver 112.

The device information 508 can include information associated with an implantation-independent attribute of an implantable system such as an IMD or its associated implantable components. The device information 508 can include information related to a manufacturer of the IMD 302 or the associated components such as a serial number, a lot number, a shipment identification, a freight identification or any other such information for use to identify the IMD 302 or any of its associated implantable components. The device information 508 can include information associated with the implantation-independent attribute of the electrodes coupled to a lead such as the lead 308 or the lead 210. The device information can include manufacturing information or identification information of the electrodes, model and serial numbers of the electrodes, shipping information. Such type of information can be useful in identifying electrodes from separate manufacturers. The device information can include electrodes usage record such as the data about whether a particular electrode has any product recall history.

The device information 508 can include a device manual that can contain a detailed description of various parameters including dimensional information associated with one or more geometrical dimensions of the IMD or any implantable component, usage or safety instructions, mechanical specifications such as a diameter of the lead, physical characteristics or electrical characteristics of the electrodes, and other device information which can assist a healthcare provide (e.g., a physician) to assess the functionality of the IMD or the associated components. The RFID circuit 310 can be configured to provide the device information 508 during an interrogation that can be initiated by the physician while performing a medical procedure on the patient 104. The device information 508 can be communicated to the remote transceiver 112 so that the physician can quickly and accurately identify the IMD and the associated components of the IMD.

The performance information 510 can include information associated with one or more performance parameters of the electrode(s) of the lead such as the lead 308 or the lead 210. The performance parameters can include predetermined range of impedance values (e.g., upper and lower limits) for the respective lead between specified electrodes when a particular therapy (e.g., a CRM therapy or a neural stimulation therapy) is delivered to the patient 104. The performance parameters include variations in the resistivity of the electrodes across different populations. For example, because electrodes similar to the electrode of the lead 308 can perform differently across different population of patients over time, a specific performance parameter (e.g., resistivity) of an electrode can be different for a patient population in an age group 25-35 and a patient population in the age group 55 or above. Accordingly, the performance information 510 including the variations in the resistivity of the electrodes across different populations can be provided to the physician to assist the physician to select a particular value or a range of values of a resistivity of the electrodes for a given patient 104. Similarly, the performance information 510 can include information associated with other performance parameters associated with a population of other electrodes or other electronics units in use. These other electrodes or electronics units can be used in other ambulatory patients.

The performance information 510 can be associated with a specific target site of implantation of the electrodes of the lead 308 within the body of the patient 104. Based on disorders associated with the patient 104, the lead (e.g., the lead 308) that includes one or more electrodes can be implanted at various sites within the body such as inside or on the surface of a heart for delivering the CRM therapy, or at or near a neural target for delivering the neural stimulation therapy to the patient 104. In an example, one of the performance parameters can correspond to a conductivity measurement associated with an electrode, and the performance information 510 can include a measurement of conductivity between the electrode and the target site of the implantation of the electrodes. The performance parameter can correspond to a resistivity measurement, and the performance information 510 can include resistivity of the electrode in conduction to the target site. The performance information 510 can include impedance values associated with the electrode such as impedance between the electrode and the target site, impedance between two electrodes, impedance between an electrode and a shunt, or impedance measured inside the body the patient 104 by one or more electrodes.

The performance information 510 can include information regarding a performance curve that can identify how the value of the performance parameter can vary with time. Generally, the IMD and the associated components such as the lead 308 can wear over time due to usage. As a result, the performance parameters associated with the IMD and associated components can vary over time. The performance curve that depicts variations in the impedance values, conductivity values, resistivity values, or other performance parameters associated with the lead over time can be included in the performance information 510. The performance curve can include distribution of intrinsic amplitude values, distribution of pacing volcircuite thresholds, distribution of lead resistance values, distribution of electrode conductance values and the like over a period of time. Data associated with the performance curves can be stored in the memory 504 in a form of performance distribution data. The performance distribution data can be generated and stored in the memory 504 in a specified data structure such as a lookup table or an association map. The performance distribution data can include a pre-determined method such as an equation or procedure for determining the value of the performance parameter. The performance distribution data can be created by a group of physicians, patients, medical representatives, experts, technicians and the like in a database that can be accessible through the computing system 116. The performance information 510 can facilitate in assessment of the performance of the IMD or the associated components when the physician initiates a testing procedure for testing and configuration of the IMD 302 such as during a medical procedure.

The testing information 512 can include a program logic that can detect whether the IMD or the associated components such as the lead 308 operates as per the information available in the performance information 510. The program logic can comprise a script-code that can be executed using any of software or a firmware associated with the IMD. The program logic can be coded using any of the available software or firmware related programming languages including, but not limited to Python, Perl, MATLAB, or Ruby. The physician can access the testing information 512 to initiate performance testing of the IMD 302 or the associated components for one or more performance parameters. The testing results can be evaluated using the performance information 510 such as to enable the physician to effectively deliver the therapy to the patient 104. Such type of performance assessment of the IMD 302 or the associated components can assist in increasing efficiency of the medical procedures associated with configuration and testing of the implantable components as the components can be made self-equipped with the performance information 510.

The RFID circuit 310 can be configured to communicate with the remote transceiver 112 that can transmit information to and/or receive information from the RFID circuit 310. The remote transceiver 112 can include a programmer or a programming unit that can communicate with the RFID circuit 310. The remote transceiver 112 can be configured in accordance with the information stored in the RFID circuit 310. It can automatically perform regular monitoring of performance related information of the implantable components. This can be done without requiring testing procedures, which can be expensive.

The remote transceiver 112 can enter a communication session with the RFID circuit 310 upon receiving a command such as an initiation of an interrogation session. The interrogation session can be initiated automatically and by the physician. The RFID circuit 310 can be instructed to communicate one or more of the device information 508, the performance information 510, and the testing information 512. This can be communicated to the remote transceiver 112. Communication can be through a wired or a wireless communication link. The wireless communication link can include a near-filed or a far-field communication link. The wired communication link can include a conductor coupled to the lead 308 of the IMD 302. The remote transceiver 112 can be configured to monitor the performance parameter of the implantable components such as the electrode using at least one of testing information 512 and the performance information 510. The remote transceiver 112 can be configured to couple to a remote computing system such as to communicate the monitored performance of the implantable components to the remote computing system 116 that can be accessed by healthcare providers (e.g., physicians or medical experts).

The RFID circuit 310 can be an active RFID circuit that can include a power source for establishing communication session with the remote transceiver 112. The RFID circuit 310 can be a passive RFID circuit including an energy coupler for wirelessly coupling electromagnetic, ultrasonic, or optical energy delivered by the remote transceiver 112. The power source can be provided by the external transceiver 112. The RFID circuit 310 can be powered up using a power source such as a battery of the IMD 302 or using a stimulation signal provided by the IMD 302. The RFID circuit 310 can include a circuit configured to harvest energy from the sources intrinsic to the patient 104, such as the biological signals generated from or within the body of the patient 104 including body motion, body heat, breathing, heartbeat, or blood pressure of the patient 104. The RFID circuit 310 can be powered up using any one of the aforementioned power sources regularly or at certain times such as during an interrogation session with the remote transceiver 112.

Figure 6:
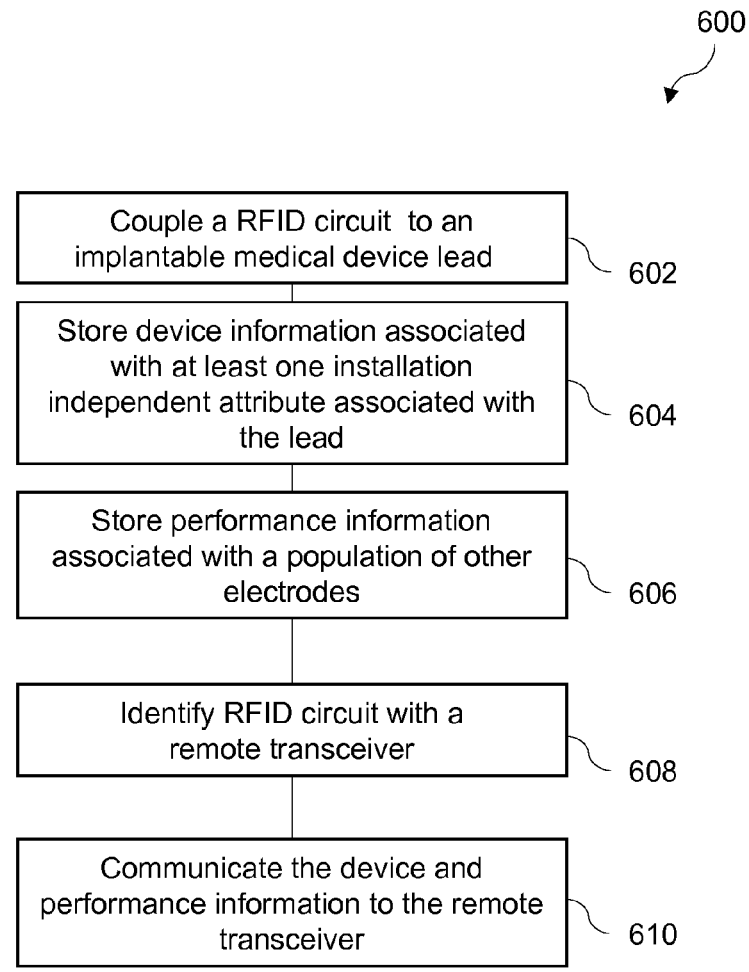
FIG. 6 illustrates an example of a method of communicating device information and performance information from an RFID circuit associated with the implantable lead to a remote transceiver.

FIG. 6 shows an example of a method 600 of communicating device information and performance information from an RFID circuit associated with an implantable lead to a remote transceiver 112. At 602, the RFID circuit is coupled to the implantable medical device lead. The RFID circuit can be coupled to the lead by an electrical or a mechanical arrangement and the implantable lead can be coupled to an implantable medical device (e.g., the IMD 302). The RFID circuit can be attached on the outer surface of the implantable lead, or can be embedded within the implantable lead. The RFID circuit can also be coupled to the implantable lead using the electrical conductors of the implantable lead. The IMD can be configured to provide power to the RFID circuit through the electrical stimulation signals sent by the IMD to the implantable lead. The RFID circuit can be powered up using energy obtained from a therapeutic shock that can be delivered by the IMD while delivering a therapy to a patient. The RFID circuit can be powered up using the implantable components associated with the IMD. In an example, the RFID circuit can be powered up using energy harvested from the biological signals from the patient. Once powered up, the RFID circuit can be accessed for storing or retrieving information associated with the implantable lead.

At 604, the device information is stored in the RFID circuit. The device information can be associated with an implantation-independent attribute of the implantable lead and the implantation-independent attribute of the implantable lead can include but is not limited to, lead manufacturer information, lead expiration data, lead wire model number or serial number, lead dimensions and the like. The implantable medical device lead can include one or more electrodes such as to deliver stimulation energy to one or more bodily tissues of the patient while delivering the therapy to treat disorders associated with the patient.

At 606, performance information associated with a population of electrodes in use, including other electrodes coupled to the implantable lead is stored in the RFID circuit. The population performance information can include trend data related to any of the performance parameters of the electrodes of the implantable lead associated with the population of other electrodes. The population of other electrodes, or electronics units, can be used in other ambulatory patients. The population performance information can include, but is not limited to, variations in pacing threshold values, an intrinsic amplitude, a lead impedance, a pacing pulse width, P/R wave amplitude slew rate, defibrillation energy or any other such information associated with the population of other electrodes. The population performance information can be stored in the form of distribution of any performance parameter over time. In an example, the performance information can also include a lead score or grade based on the lead performance with respect to the population data. As already discussed above, the IMD can be configured to include one or more RFID circuits such as to store specific information associated with the one or more implantable leads of the IMD.

At 608, the RFID circuit is identified by at least one remote transceiver such as for establishing a communication session with the RFID circuit via a wired or a wireless communication link. The RFID circuit can be packaged in the form of an integrated circuit with an attached antenna for wireless signal reception and transmission. The remote transceiver can include a RFID reader, a programmer, or a programming unit such as the transceiver 112. The remote transceiver can send an identification signal to the RFID through the communication link. Upon receiving the signal from the remote transceiver, the RFID circuit can be configured to communicate identification information to the remote transceiver so that the remote transceiver can identify association of the RFID circuit to the respective implantable lead of the IMD. The RFID circuit can be automatically identified when the implantable lead is within a specified distance of the remote transceiver.

The RFID circuit can be configured to communicate with, and to be identified by, at least two remote transceivers each including unique software and/or unique hardware. For example, the at least two remote transceivers can be from different manufactures or vendors. The RFID circuit can be configured to communicate to at least one remote transceiver at least one implantation-independent attribute. The RFID circuit can be configured such that the information received from the RFID circuit is compatible with the at least two remote transceivers, even though the remote transceivers can be functionally different.

Upon identification of the RFID circuit, at 610, the device information and the performance information stored in the RFID circuit can be communicated to the remote transceiver. The physician can create an interrogation session to extract the information available in the RFID circuit of the implantable lead. During such an interrogation session, the remote transceiver can obtain information from the RFID circuit, or can store information in a memory of the RFID circuit. The remote transceiver can be operatively coupled to a remote computing system which can be capable of relaying the information obtained from the RFID circuit to a plurality of external systems, such as to a remote database, a lead manufacturer's website, a patient management system, a remote server, or any other such systems.

The device information and the performance information stored in the RFID circuit can be retrieved by at least two remote transceivers at 610, so that the implantable lead can be adapted to operate using any of the two different types of the remote transceivers. In an example, the two or more remote transceivers can operate under a common protocol of extracting information from the RFID circuit so that each of the remote transceiver can program the implantable lead using the extracted information. This can facilitate flexibility in the implantation of medical systems so that the physician can program the implantable lead from different vendors using a single remote transceiver.

The method 600 can also include programming the RFID circuit with the information such as an up-to-date device and performance information and the like using the remote transceiver. The remote transceiver can be configured to receive the up-to-date information from the remote computing system and accordingly, the remote transceiver can program the RFID circuit using a wired or a wireless communication link. The RFID circuit can be programmed using one or more conductors of the implantable lead such that the conductors can be in contact with other electronic circuits that can be adapted to program the RFID circuit. In another example, the RFID circuit can be programmed over a conductor of the implantable lead coupled to implantable electronics such as the pulse generator of the IMD. The remote transceiver 112 can be configured to retrieve performance information for a specific patient from the remote computing system and program the RFID circuit using the retrieved performance information.

The method 600 can also include programming the RFID circuit with the information received from a communication module so as to re-program the RFID circuit with an up-to-date device and performance information of the implantable lead. The communication module can enable the programmer such as the remote transceiver 112 or the remote computing system 116 to wirelessly program the RFID circuit using a wireless communication link. The communication module can be a wireless near field communication module or a wireless far field communication module. The wireless far field communication module can be a satellite communication module.

The method 600 can also include a programmer for storing any of the device information or the performance information into the RFID circuit. The programmer can be configured to obtain the device information or the performance information from a network computer such as the computing system 116. The device information or the performance information can be stored in the network computer by the patient. In some examples, the device information or the performance information can be stored in the network computer by a healthcare provider such as a medical expert. The medical expert can periodically update such information as part of a continuous research process. The RFID circuit can then be programmed using this up-to-date information available in the network computer so as to assist the physician to control the operations of the IMD while delivering a therapy to the patient.

Figure 7:
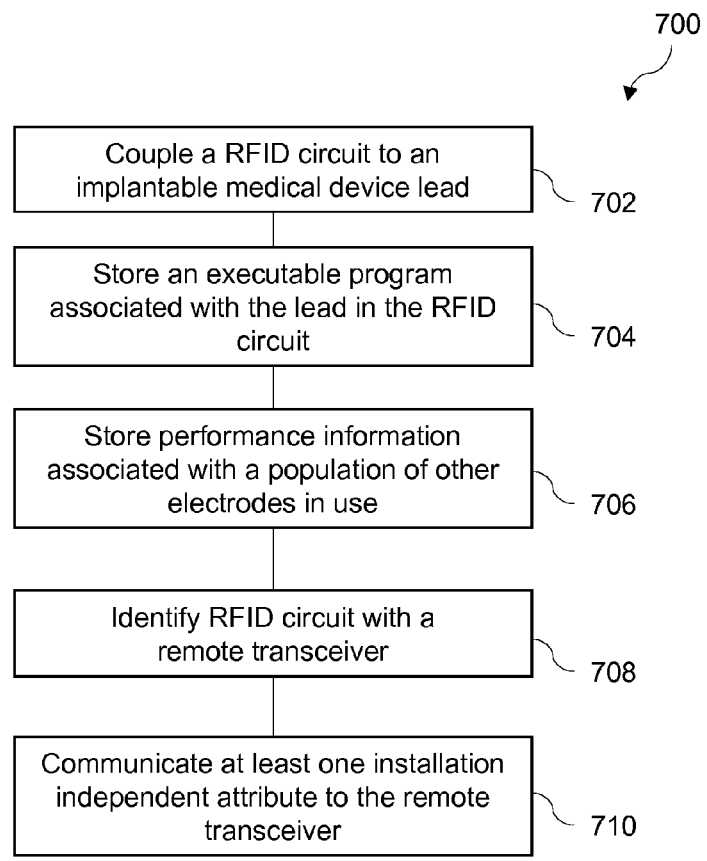
FIG. 7 illustrates an example of a method of communicating at least one implantation-independent attribute of the implantable medical device lead to a remote transceiver.

FIG. 7 shows an example of a method 700 of communicating an at least one implantation-independent attribute of the implantable medical device lead to the remote transceiver 112. At 702, an RFID circuit is coupled to the implantable medical device lead. The RFID circuit can be coupled to the lead by an electrical or a mechanical arrangement and the implantable lead can be coupled to an IMD such as the IMD 302, such as to deliver a therapy to the patient. Examples of the therapy include a CRM therapy, a neural stimulation therapy, or any other therapies provided by the IMD to the patient. At 704, an executable program associated with the implantable medical device lead can be stored in the RFID circuit. The executable program associated with the lead can include programming instructions that can facilitate evaluation of the implantable medical device lead such as to provide performance related information of the implantable medical device lead to the IMD. The executable program can also include interpreted script, which can be optionally encrypted and digitally signed to support confidentiality and checks for code authenticity.

At 706, performance information associated with a population of electrodes in use, including electrodes that can be other than the electrodes coupled to the implantable medical device lead, can be stored in the RFID circuit. The performance information may include additional or similar information associated with the performance of the implantable medical device lead of method 700. The RFID circuit can be configured as a memory circuit for storing the executable program and the performance information. Once stored, the information can be retrieved from the RFID circuit for a later use by the physician. At 708, the RFID circuit can be identified with a remote transceiver. The remote transceiver can be a RFID reader, a programmer, or a programming unit that can be external to the IMD and the implantable lead. In another example, the IMD can itself be configured to couple to the remote transceiver 112 so that the RFID circuit can be identified using the IMD and the remote transceiver 112. As discussed herein, identifying the RFID circuit can include sending the identification signal to the RFID circuit from the remote transceiver 112. Upon identification of the RFID circuit, at 710, the at least one implantation-independent attribute of the implantable medical device lead can be communicated to the remote transceiver 112.

The method 700 can include executing the executable program, such as a script or an executable code segment, associated with the implantable medical device lead on the IMD. The executable program can also include interpreted script, which can be optionally encrypted and digitally signed to support confidentiality and checks for code authenticity. The execution of the program can assist in programming of the IMD based on the information available after the execution of the executable program such that the implantable medical device lead can be configured as per the instructions carried with the lead itself resulting into a creation of a self-configuring lead. In this example, the lead can be used across a plurality of different programmers and plurality of lead configuring software as the lead itself provides information related to its programming that can be stored in the executable program. The plurality of different programmers merely needs to execute the executable program. This can reduce lead configuration costs and at the same time can enable a less trained personnel to correctly identify and configure the lead. For example, a medical representative from an insurance agency who may need to identify the lead model and functional parameters can simply plug-in the lead into an implantable system, and then using the lead's RFID circuit and the external transceiver, quickly obtain lead configuration and performance information.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. The code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The present inventor has contemplated various examples of the systems and methods discussed in this document. Example 1 can include or use subject matter, such as an apparatus, that can include or use a system for implanting into a target site. The system can comprise an elongated lead body, a signal conductor, an electrode affixed to the lead body, an electrode circuit in communication with the electrode, and at least one radio frequency identification (RFID) circuit attached to the lead in communication with the electrode circuit.

Example 2 can include, or can optionally be combined with the subject matter of Example 1, to optionally include performance information associated with implantation at a specified target site in common across the population.

Example 3 can include, or can optionally be combined with the subject matter of one or any combination of Examples 1 or 2 to optionally include dimensional information associated with one or more geometric dimensions of the system.

Example 4 can include, or can optionally be combined with the subject matter of one or any combination of Examples 1 through 3 to optionally include device information including a manual.

Example 5 can include, or can optionally be combined with the subject matter of one or any combination of Examples 1 through 4 to optionally include performance parameter including one or more of conductivity, resistivity, or impedance such as impedance between the electrode and the target site or impedance between the electrode and a shunt.

Example 6 can include, or can optionally be combined with the subject matter of one or any combination of Examples 1 through 5 to optionally include an electrode circuit that can monitor the performance parameter of the electrode, or to store the performance information associated with the performance parameter.

Example 7 can include, or can optionally be combined with the subject matter of one or any combination of Examples 1 through 6 to optionally include at least one RFID circuit which can be powered by a power source of at least one of the plurality of implantable components, a signal from an implantable component, or an external device.

Example 8 can include, or can optionally be combined with the subject matter of one or any combination of Examples 1 through 7 to optionally include device information such as manufacturing information or system identification information.

Example 9 can include a method, a means for performing acts, or a device readable medium including instructions that, when performed by the device, can cause the device to perform acts. The method can comprise coupling a radio frequency identification (RFID) circuit to an implantable medical device lead, storing device information associated with at least one implantation-independent attribute, storing performance information, identifying the RFID circuit with a remote transceiver, and communicating the device information and the performance information to the remote transceiver upon identification of the RFID circuit.

Example 10 can include, or can optionally be combined with the subject matter of Example 9, to optionally include coupling the lead to an implantable device.

Example 11 can include, or can optionally be combined with the subject matter of one or any combination of Examples 9 or 10 to optionally include powering the RFID circuit with energy from the implantable device.

Example 12 can include, or can optionally be combined with the subject matter of one or any combination of Examples 9 through 11 to optionally include powering the RFID circuit with energy from a therapeutic shock provided the implantable device.

Example 13 can include, or can optionally be combined with the subject matter of one or any combination of Examples 9 through 12 to optionally include communicating at least one implantation-independent attribute to another remote transceiver. The remote transceiver and the other remote transceiver can each include unique software or hardware.

Example 14 can include, or can optionally be combined with the subject matter of one or any combination of Examples 9 through 13 to optionally include programming the RFID circuit with information from the remote transceiver. The programming includes wired or wireless programming.

Example 15 can include, or can optionally be combined with the subject matter of one or any combination of Examples 9 through 14 to optionally include a wireless near field communication module or a wireless far field communication module such as a satellite.

Example 16 can include, or can optionally be combined with the subject matter of one or any combination of Examples 9 through 15 to optionally include programming the RFID with performance information associated with a patient.

Example 17 can include, or can optionally be combined with the subject matter of one or any combination of Examples 9 through 16 to optionally include automatically identifying the RFID circuit when the lead is within a specified distance of the remote transceiver.

Example 18 can include, or can optionally be combined with the subject matter of one or any combination of Examples 9 through 17 to optionally include communicating the at least one implantation-independent attribute to the RFID circuit wirelessly with a programmer circuit.

Example 19 can include, or can optionally be combined with the subject matter of one or any combination of Examples 9 through 18 to optionally include providing the programmer circuit with the performance information via a network.

Example 20 can include, or can optionally be combined with the subject matter of one or any combination of Examples 9 through 19 to optionally include storing the performance information in a network computer in communication with the programmer circuit via the network.

Example 21 can include a method, a means for performing acts, or a device readable medium including instructions that, when performed by the device, can cause the device to perform acts. The method can comprise coupling a radio frequency identification (RFID) circuit to an implantable medical device lead, storing an executable program, associated with the implantable medical device lead, storing in the RFID circuit performance information associated with performance information associated with a population of other electrodes in use, identifying the RFID circuit with a remote transceiver, and communicating the at least one implantation-independent attribute to the remote transceiver upon identification of the RFID circuit.

Example 22 can include, or can optionally be combined with the subject matter of Example 21, to optionally include coupling the lead to an implantable device.

Example 23 can include, or can optionally be combined with the subject matter of one or any combination of Examples 21 or 22 to optionally include executing the executable program on an implantable device to program the implantable device.

The above description is intended to be illustrative, and not restrictive. The above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system for implantation into a target site, comprising:
  an implantable electronics unit including:
    a biocompatible exterior portion;
    an electronic circuit, including device information associated with an implantation-independent attribute of the implantable electronics unit and performance information associated with a performance parameter associated with at least one other implantable electronics unit in use external to the target site; and
    at least one radio frequency identification (RFID) circuit attached to the implantable electronics unit in communication with the electronic circuit, the RFID circuit configured to communicate the device information and the performance information to a remote transceiver during interrogation.

2. The system of claim 1, wherein the implantable electronics unit includes an implantable lead comprising:
  an elongated lead body including a biocompatible exterior portion;
  a signal conductor extending from a proximal portion of the lead body to a distal portion of the lead;
  an electrode affixed to the lead body in electrical communication with the signal conductor;
  wherein the electronic circuit includes an electrode circuit in electrical communication with the electrode and including device information associated with an implantation-independent attribute of the electrode and including performance information associated with performance parameter associated with an electrode in use with a separate implantable electronics unit; and
  at least one radio frequency identification (RFID) circuit attached to the lead in communication with the electrode circuit, the RFID circuit configured to communicate the device information and performance information during interrogation.

3. The system of claim 1, wherein the performance information is associated with implantation at a specified target site in common across the population.

4. The system of claim 1, wherein the device information includes a manual.

5. The system of claim 1, wherein the device information includes manufacturing information.

6. The system of claim 1, wherein the device information includes system identification information.

7. The system of claim 1, wherein the performance information includes one or more electrical physiologic measurements including electrogram amplitude, pacing threshold, or impedance.

8. The system of claim 1, wherein the performance information includes one or more mechanical physiologic measurements including stress, strain, movement, or pressure.

9. The system of claim 1, wherein the electronic circuit is to monitor the performance parameter of an electrode.

10. The system of claim 1, wherein the electronic circuit is to store the performance information associated with the performance parameter.

11. The system of claim 1, wherein the at least one RFID circuit is powered by a power source of at least one of a plurality of implantable components.

12. The system of claim 1, wherein the at least one RFID circuit is powered by an external device.

13. The system of claim 1, wherein the device information includes at least one of manufacturing information or system identification information.

14. A method, comprising:
coupling a radio frequency identification (RFID) circuit to an implantable electronics unit;
storing, in the RFID circuit, device information associated with at least one implantation-independent attribute of the implantable electronics unit;
storing, in the RFID circuit, performance information associated with a performance parameter associated with a population of other implantable electronics units in use;
identifying the RFID circuit with a remote transceiver; and
upon identification of the RFID circuit, communicating the device information and the performance information to the remote transceiver.

15. The method of claim 14, comprising coupling the implantable electronics unit to an implantable device.

16. The method of claim 15, comprising powering the RFID circuit with energy from the implantable device.

17. The method of claim 14, comprising communicating the at least one implantation-independent attribute to another remote transceiver wherein the remote transceiver and the other remote transceiver each include unique software.

18. The method of claim 14, comprising programming the RFID circuit with information from the remote transceiver.

19. The method of claim 14, wherein storing the device information includes communicating the at least one implantation-independent attribute to the RFID circuit wirelessly with a programmer circuit.

20. A method, comprising:
coupling a radio frequency identification (RFID) circuit to an implantable medical device lead;
storing, in the RFID circuit, an executable program associated with the implantable medical device lead;
storing, in the RFID circuit, performance information associated with performance information associated with a population of other leads in use;
identifying the RFID circuit with a remote transceiver; and
upon identification of the RFID circuit, communicating the at least one implantation-independent attribute to the remote transceiver.

* * * * *